US00PP07947P

United States Patent [19]

Zaiger et al.

[11] Patent Number: Plant 7,947

[45] Date of Patent: Aug. 18, 1992

[54] NECTARINE TREE JOLLY RED GIANT

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 640,864

[22] Filed: Jan. 14, 1991

[51] Int. Cl.[5] ..... A01H 5/00

[52] U.S. Cl. ..... Plt./41.3

[58] Field of Search ..... Plt./41

*Primary Examiner*—James R. Feyrer

[57] ABSTRACT

A new and distinct variety of nectarine tree which has the following outstanding features that are desirable in a new variety:

1. Very large size freestone fruit.
2. Fruit with excellent flavor and eating quality.
3. Vigorous upright growth.
4. Heavy and regular production of fruit.
5. Fruit with a high degree of attractive red skin color.
6. Fruit with good storage and shipping quality.

1 Drawing Sheet

ORIGIN OF THE VARIETY

The present new variety of nectarine tree was originated by us in our experimental orchard located near Modesto, Calif., as a first generation seedling from a cross between two nectarine seedlings with the field identification numbers 19G850 and 55GA798. The female parent with the identification number 19G850 originated from an open pollinated Ruby Gold Nectarine (U.S. Plant Pat. No. 3,101). The pollen parent with the identification number 55GA798 originated from a second generation cross between Flame Kist Nectarine (non-patented) and a selected nectarine seedling which originated from a cross between an open pollinated Red Grand Nectarine (U.S. Plant Pat. No. 1,060) seedling and Royal Gold Peach (U.S. Plant Pat. No. 2,663). We grew and maintained a large group of these first generation seedlings under careful observation and the present variety which exhibited the distinctive desirable characteristics described above was selected for asexual reproduction and commercialization.

ASEXUAL REPRODUCTION OF THE VARIETY

The new and distinct variety of nectarine tree was asexually propagated by budding by us in our experimental orchard located near Modesto, Calif., and shows that such reproductions run true to the original tree and are established and transmitted through succeeding propagations.

SUMMARY OF THE VARIETY

The herein described variety of nectarine tree is of large size, vigorous upright growth and a productive and regular bearer of very large, firm, yellow flesh, freestone fruit with excellent eating quality. The fruit is further characterized by its relative uniform maturity on the tree, a high degree of attractive red skin color and good storage and shipping qualities. In comparison to the Red Grand Nectarine (U.S. Plant Pat. No. 1,060) the fruit of the present variety ripens in approximately the same maturity season but is freestone instead of clingstone, has a higher degree of attractive red skin color, and has heavier production with larger size fruit.

BRIEF DESCRIPTION OF THE PHOTOGRAPHS

The photographic reproductions in color are of typical specimens of the foliage and firm ripe fruit of the present variety of nectarine tree. These illustrations show the upper and lower surface of the leaves, the exterior and sectional view of the fruit, with a fruit being divided in its suture plane to show flesh coloration and a stone remaining in place. The photographic illustrations were taken shortly after the fruit was picked at maturity and the colors are as nearly true as is reasonably possible in a color representation of this type.

DESCRIPTION OF THE VARIETY

The following is a botanical detailed description of the present variety of nectarine tree, its flowers, foliage and fruit as based on observations of specimens grown near Modesto, Calif., with color terminology (except those in common terms) in referenced to Reinhold Color Atlas by A. Kornerup and J. H. Wanscher.

Tree:
- *Size.*—Large.
- *Vigor.*—Vigorous.
- *Density.*—Medium dense.
- *Form.*—Upright.
- *Production.*—Very productive.
- *Bearer.*—Regular.

Trunk:
- *Size.*—Large.
- *Texture.*—Medium shaggy.
- *Color.*—Brown to grayish brown (6-E-4) to (6-E-6).

Branches:
- *Size.*—Medium.
- *Texture.*—Smooth to medium rough.
- *Lenticels.*—Small size. Few in number.
- *Color.*—New growth reddish brown (8-E-6). Mature growth brown (7-D-5).

Leaves
- *Size.*—Large. Average length — 6¾". Average width — 1⅝".
- *Form.*—Lanceolate. Pointed.
- *Margin.*—Crenate.
- *Texture.*—Relatively smooth.
- *Thickness.*—Medium.
- *Petiole.*—Medium length. Medium thickness.

*Glands.*—Number varies from 1 to 6. Average number 2. Reniform. Positioned on base of leaf blade and upper portion of petiole.

*Color.*—Upper surface — green to dark green (27-F-5) to (27-F-7). Lower surface — dull green to light green (27-E-4) to (27-E-6).

Flower buds:

*Size.*—Medium to large.

*Length.*—Medium.

*Form.*—Plump.

Flowers:

*Size.*—Large — showy.

*Blooming period.*—Date of first bloom, Mar. 3, 1990. Date of full bloom, Mar. 7, 1990. Varies slightly with climatic conditions.

*Pollen.*—Present — self fertile.

*Color.*—Pink.

Fruit:

*Maturity when described.*—Firm ripe.

*Date of first picking.*—Jul. 17, 1990.

*Date of last picking.*—Jul. 23, 1990.

*Size.*—Large — comparatively uniform. Average diameter axially — 3⅛" to 3⅜". Average transversely in suture plane — 3" to 3½".

*Form.*—Nearly globose, slightly elongated in suture plane.

*Suture.*—Shallow, nearly rounded, extends from base to just beyond apex.

*Ventral surface.*—Usually rounded.

*Cavity.*—Nearly round, only slightly elongated in suture plane. Average depth — ⅝". Average breadth — 1".

*Apex.*—Varies from nearly round to slight pistil point.

*Base.*—Only slightly retuse.

Skin:

*Thickness.*—Medium.

*Texture.*—Medium tough, tenacious to the flesh.

*Tendency to crack.*—None.

*Down.*—Wanting.

*Color.*—Yellow to golden yellow ground color (4-A-5) to (5-A-5). Overspread with red to lobster red (9-C-8) to (9-B-8).

Flesh:

*Ripens.*—Evenly.

*Texture.*—Firm.

*Amygdalin.*—Undetected.

*Juice.*—Moderate.

*Fibers.*—Medium size, tender.

*Aroma.*—Moderate.

*Flavor.*—Excellent, good balance between acid and sugar.

*Eating quality.*—Excellent.

*Color.*—Golden yellow to light orange (4-A-5) to (5-A-5). Pit cavity — α light red to orange red (9-A-6) to (9-A-7). Red streaks bleeding into flesh from pit cavity, heavier toward apex.

Stone:

*Type.*—Freestone.

*Size.*—Large. Average length — 1½". Average breadth — 1 1/16". Average thickness — ¾".

*Form.*—Oval to obovate.

*Base.*—Usually rounded, varies from rounded to straight.

*Apex.*—Acuminate.

*Sides.*—Equal to unequal.

*Surface.*—Irregularly furrowed toward apex, pitted toward base. Ridges usually rounded. Pit cavities vary from elongated to round.

*Tendency to split.*—None.

*Color.*—Brown to dark brown (6-E-6) to (6-E-8).

Use:

*Markets.*—Local and long distance. Dessert.

Keeping quality: Good.

Shipping quality: Good.

The present variety of nectarine tree, its flowers and fruit herein described may vary in slight detail due to climatic, soil types and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, upright, vigorous growth and a productive and regular bearer of very large, firm, yellow flesh, freestone fruit with excellent flavor and eating quality; the new variety is further characterized in comparison to Red Grand Nectarine (U.S. Plant Pat. No. 1,060) as producing larger fruit, being heavier in production, having fruit with a higher degree of attractive red skin color, which are freestone instead of clingstone.

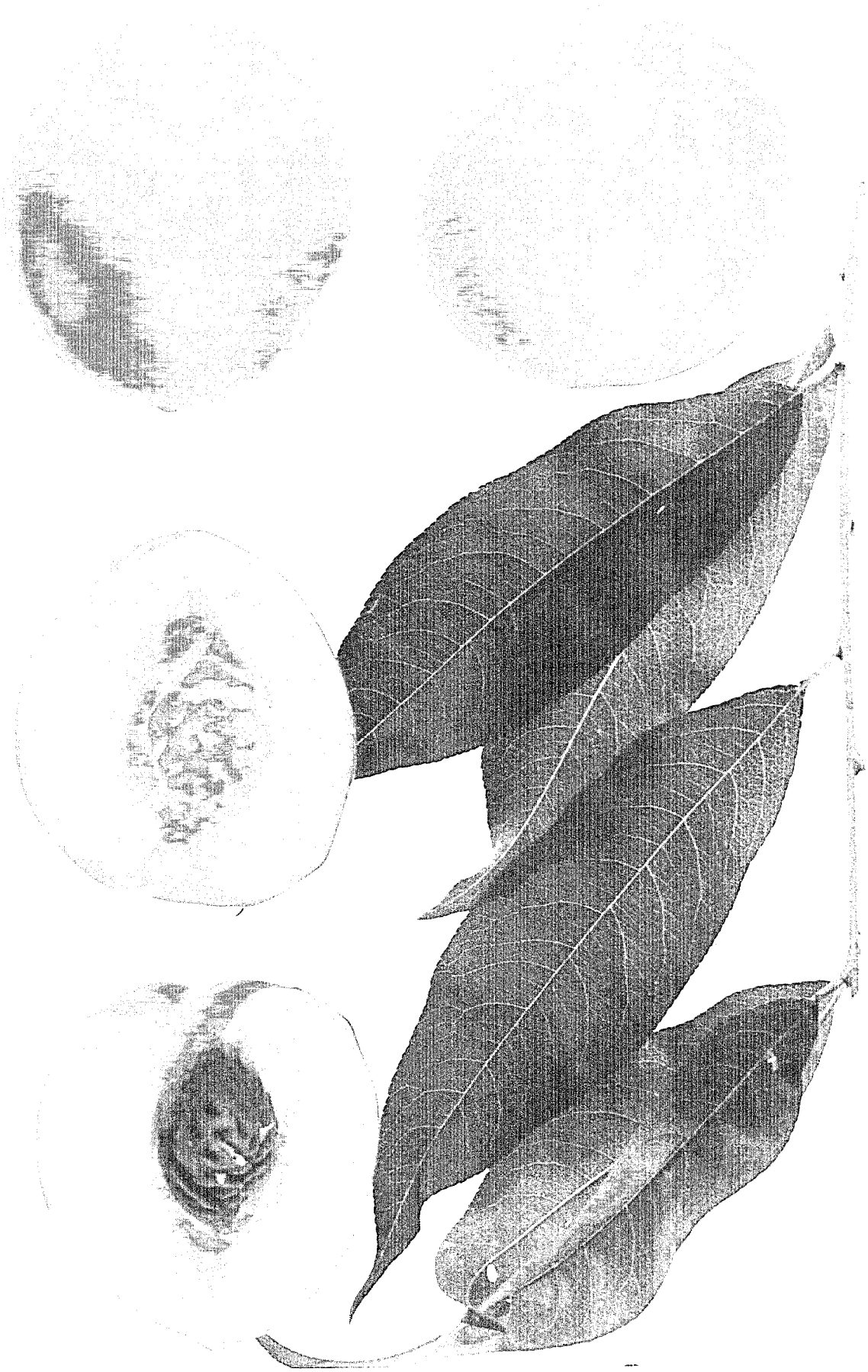

* * * * *